(12) United States Patent
Chen

(10) Patent No.: US 6,689,618 B1
(45) Date of Patent: Feb. 10, 2004

(54) METHOD AND TEST STRIP OF DETECTING OXIDIZING ADULTERANT IN URINE

(76) Inventor: Shuenn Tzong Chen, 2305 Pinehurst Dr., Tustin, CA (US) 92782

( * ) Notice: Subject to any disclaimer, the term of this patent is extended or adjusted under 35 U.S.C. 154(b) by 0 days.

(21) Appl. No.: 09/542,512

(22) Filed: Apr. 3, 2000

(51) Int. Cl.$^7$ .............................................. G01N 33/00
(52) U.S. Cl. ...................... 436/135; 436/124; 436/125; 436/95; 435/4; 435/10; 435/11; 435/14; 435/28
(58) Field of Search ................................ 436/124, 125, 436/135, 95; 435/4, 28, 10, 11, 14

(56) References Cited

U.S. PATENT DOCUMENTS

| | | | |
|---|---|---|---|
| 3,290,228 A | 12/1966 | Butters et al. | |
| 4,134,793 A | 1/1979 | Terada et al. | |
| 4,215,197 A | 7/1980 | Tarbutton | |
| 4,380,585 A | 4/1983 | Magers et al. | |
| 4,578,361 A | 3/1986 | Siedel et al. | |
| 4,769,215 A | 9/1988 | Ehrenkranz | |
| 4,895,798 A | 1/1990 | Charlton et al. | |
| 5,069,878 A | 12/1991 | Ehrenkranz | |
| 5,203,327 A | * 4/1993 | Schoendorfer et al. | 600/362 |
| 5,318,894 A | 6/1994 | Pugia | |
| 5,464,775 A | 11/1995 | Smith | |
| 5,464,777 A | 11/1995 | Yip | |
| 5,491,094 A | 2/1996 | Ramana et al. | |
| 5,610,073 A | 3/1997 | Chu et al. | |
| 5,676,144 A | 10/1997 | Schoendorfer | |
| 5,710,012 A | 1/1998 | Nikolyukin et al. | |
| 5,733,787 A | 3/1998 | Messenger et al. | |
| 5,753,451 A | 5/1998 | Smith | |
| 5,783,149 A | 7/1998 | Serrat | |
| 5,801,060 A | 9/1998 | Smith | |
| 5,888,758 A | 3/1999 | Wu | |
| 5,976,895 A | * 11/1999 | Cipkowski | 422/102 |
| 5,981,204 A | * 11/1999 | Johnson et al. | 435/7.1 |
| 6,303,384 B1 | * 10/2001 | Mills et al. | 436/111 |

OTHER PUBLICATIONS

The Journal of Biological Chemistry vol. 257, No. 7, Issue of Apr. 10, pp. 3669–3675, 1982: "The Horseradish Peroxidase–catalyzed oxidation of 3,5,3', 5'—Tetramethylbenzidine".

* cited by examiner

*Primary Examiner*—Jill Warden
*Assistant Examiner*—Latoya Cross
(74) *Attorney, Agent, or Firm*—Myers Dawes Andras & Sherman LLP; Vic Y. Lin; Joseph C. Andras

(57) ABSTRACT

A single reagent system and a method to detect and measure oxidizing adulterants in bodily fluid being screened for drugs of abuse are disclosed. The system comprising a strip containing 0.05 to 0.2 micromole/25 sq. mm. of a benzidine derivative and is used to detect sodium hypochlorite (bleach), chlorine, hydrogen peroxide, sodium bromide, sodium iodide, sodium nitrite, and pyridinium chlorochromate adulterants in urine, sweat, saliva, blood or other bodily fluids during screening for drugs of abuse.

10 Claims, 1 Drawing Sheet

METHOD AND TEST STRIP OF DETECTING OXIDIZING ADULTERANT IN URINE

1. FIELD OF THE INVENTION

The present invention relates to a single reagent system and method designed to detect and measure oxidizing adulterants in urine, sweat, saliva, blood or other bodily fluids being screened for drugs of abuse. Specifically, the present invention is directed to detect and measure sodium hypochlorite (bleach), chlorine, hydrogen peroxide, sodium bromide, sodium iodide, sodium nitrite and pyridinium chlorochromate adulterants in urine during screening for drugs of abuse.

2. BACKGROUND OF THE INVENTION

As the use of illicit drugs in public, workplace, sports and the like has grown, public concern for the health and safety of individuals and the negative impact of such drugs use on productivity of industry has grown as well. Such concern obligated the use of analysis of urine, sweat, saliva, blood, or other bodily fluids, as a way to detect and defer drug use. Such testing for drugs of abuse in industry for prospective and current employees, particularly government employees, military personnel, professional and amateur athletes, truck drivers, pilots, as well as people under supervision of the criminal justice system, has become a routine practice.

Because of the significance of a positive result in such testing commonly performed by examining an urine, sweat, saliva, blood or other bodily fluids sample, the testing procedure must withstand vigorous scrutiny. A positive test result of screening for drugs of abuse can have serious impact on the life of a person being tested. The incentive for a user to alter the test specimen is high. The users of drugs of abuse have developed ways to adulterate the collected specimen in an attempt to produce a false negative result in the drug screening test being conducted.

A drug user may affect the test results by dilution reduce the drug concentration in the urine sample; substitution with liquids such as clean (drug-free) urine, apple juice, tea, soda for the drug containing specimen; or adulteration- addition to the urine specimen of foreign substances in an attempt to invalidate the test.

Such adulteration of urine sample can be achieved by the addition of several readily available agents, including household products; i.e. bleach (sodium hypochlorite), chlorine, sodium bromide, sodium iodide, hydrogen peroxide, pyridinium chlorochromate finger nail polish remover, Visine, soap, together with commercial available adulteration products, such as "URINE-AID®" (gluteraldehyde), and "KLEA®" (sodium nitrite).

Additionally, drug users may eliminate some drugs rapidly from their bodies by altering their urinary pH. This includes using NU4Cl to hasten the elimination of phencyclidine or amphetamines from the bodies.

While the use of some in vitro adulterants can be eliminated by the direct observation of the test subject during the collection process, such direct observation is often deemed unacceptable.

Such adulteration can affect the four commonly used methods for drugs of abuse, namely: enzyme immunoassay (EIA or EMIT), lateral flow immunoassey (LFIA), radioimmunoassay (RIA) and florescent polarization Immunoassay (FPIA). Thus, clinical chemistry literature recommends that adulterants be tested prior to testing of drugs of abuse in urine samples.

Accordingly, a need exists for providing an easy and convenient manner by which to make a determination of the presence of oxidizing adulterants in urine samples prior to the testing for drugs of abuse. Particularly, the need exists to provide an easy and convenient manner to detect bleach, chlorine, sodium bromide, sodium iodide, hydrogen peroxide, sodium nitrite, and pyridinium chlorochromate in urine samples prior to the testing for drugs of abuse.

3. DESCRIPTION OF THE PRIOR ART

The patent to Ehrenkranz (U.S. Pat. No. 4,769,215) discloses a urine sample collection apparatus having ability for detecting the presence of adulterants, such as bleach, intentionally added into the urine sample to tamper or mask urine test results. The apparatus is provided with an enzyme/bleach poison detector or strip having an indicator formed from glucose oxidase, peroxidase and potassium iodide.

The patent to Smith (U.S. Pat. No. 5,464,775) discloses a method of detecting adulterants, such as bleach and gluteraldehyde, in urine samples through the use of an indicator containing essentially phenylhydrazine.

The patents to Ramana et al.(U.S. Pat. No. 5,491,404); Serrat (U.S. Pat. No. 5,783,149); and Wu (U.S. Pat. No. 5,888,758) all disclose the specific use of tetramethylbenzidine as an indicatoron a test strip (or in a kit) for detecting the presence of chlorine in water samples.

The patents to Gretton et al. (U.S. Pat. No. 3,290,228); Magers et al. (U.S. Pat. No. 4,380,585); and Chariton et al. (U.S. Pat. No. 4,895,798); all disclose the use of tetramethylbenzidine or benzidine per se for detecting glucose in body fluids, such as blood or urine.

The patents to Pugia (U.S. Pat. No. 5,318,894); and Kardos et al. (U.S. Pat. No. 5,885,789); both disclose the use of benzidine-containing compositions per se for detecting peroxidative substances such as blood in urine or other body fluids.

All of the above patents had to use very complicated and/or expensive reagent system and are troublesome to get quick and easy test results. The use of an aqueous enzyme system makes it difficult to handle and has a limited shelf life.

4. SUMMARY OF THE INVENTION

Accordingly, it is an object of the present invention to provide for a test strip- a single reagent system and a method to detect and measure oxidizing adulterants in urine or other bodily fluids, being screened for drugs of abuse.

In a preferred embodiment, a 0.1 to 0.9 g of a reagent-benzidine derivative (including o-tolidine, o-tolidine dihydrochloride, benzidine, benzidine dihydrochloride, 3,5,3',5'tetramethylbenzidine and 3,5,3',5'tetramethylbenzidine dihydrochloride) is dissolved in 100–300 ml of a pH 5 phosphate or acetate buffer, or water and (0–50 ml) 2.5 percent Gantrez (ISP Technologies Inc. manufacturer of GAF Chemicals). A filter paper such as Whatman #3 type, or a paper of cellulose base, woven or non-woven, or other materials like fiberglass, is then soaked in the solution for 0.1 to 10 minutes. The excess solution is then squeezed out and dried in an oven at 50–75 degree C for 10–30 minutes. The amount of the benzidine derivative on the test strip is calculated to be from about 0.05 to 0.2 micromole or 0.15 to 60 microgram per 25 sq. mm (millimeter).

In an alternative embodiment, the process can be accomplished by slipping the paper material in a roll configuration and then use warm air to blow dry the material instead of putting it into an oven to dry. The roll of paper is then cut into the strip for testing purposes.

During an analysis, the paper containing the dried reagent is contacted with a liquid, such as urine, to be analyzed. After the liquid has been in contact with the dried reagent for a selected time up to 15 minutes, the paper containing the dried reagent is evaluated for detecting color change.

For a solution containing 0.5% to 20% (by volume) CHLOROX® (brand sodium hypochlorite bleach) and iodide, a blue color is detected.

For a solution containing 0.05 to 10% (by weight) pyridinium chlorochromate, a reddish-brown color is detected.

For a solution of containing 10 to 30% (by weight) hydrogen peroxide, a light blue color is detected.

For a solution containing 0.01 to 10% (by weight) of sodium nitrite, a very dark blue color is detected.

Other objects and advantage of the invention will become apparent from the following detailed disclosure.

5. BRIEF DESCRIPTION OF THE DRAWING

The novel features which are believed to be characteristic of the invention are set forth with particularity in the appended claims. The invention itself, however, both as to its organization and method of operation, may best be understood by reference to the following description, taken in connection with the accompanying drawing in which:

6. DETAILED DESCRIPTION OF THE INVENTION

Figure 1:
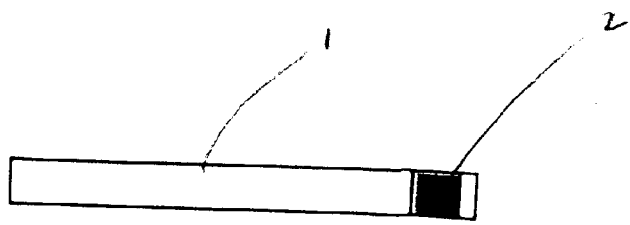
FIG. 1 is a perspective view of a test strip showing the 3,5,3',5'tetramethylbenzidine reagent for detecting oxidizing adulterants in urine.

Referring now to FIG. 1, a test-strip 1 used to detect oxidizing adulterants in urine is prepared by using about 0.5 g of the reagent-3,5,3',5'tetramethylbenzidine (TMB) dissolved in about 200 ml of a pH 5 phosphate or acetate buffer and about 2.5% Gantrez, such as polymethyl vinyl ether/ maleic anhydride copolymers. A Whatman #3 type filter paper is then soaked in the solution for about 10 minutes. The excess solution is then squeezed out and dried in an oven at about 60 degree C for about 15 minutes.

The urine for the testing is collected in a clean plastic container. No centrifuging or preservative is added to the urine sample. The paper containing the dried reagent TMB 2 is contacted with the urine to be analyzed. After the urine has been in contact with the dried reagent for about 1–5 minutes, the paper containing the dried reagent is evaluated for detecting color change.

EXAMPLE 1

Detection of Sodium Hypochlorite (Bleach)

A one volume part of aqueous 5.25% by weight sodium hypochlorite solution is diluted with the indicated volume parts of normal urine. Test strip was white prior to immersion into the testing solution. Readings were taken about 1 minute after immersion.

| Dilution | 1/10 | 1/20 | 1/50 | 1/100 | 1/200 | 1/500 |
|---|---|---|---|---|---|---|
| Color | very dark blue | dark blue | blue | light blue | very light blue | white |

EXAMPLE 2

Detection of Pyridimium Chlorochromate

The following concentrations were percentage by weight (w/w) in urine. Readings were taken 1 minute after immersion.

| Conc. | 10% | 5% | 1% | 0.5% | 0.1% | 0.05% |
|---|---|---|---|---|---|---|
| Color | Reddish brown | brown | very dark blue | dark blue | light blue | white |

EXAMPLE 3

Detection of Iodine and Sodium Iodate

The starting solution contains 2% iodine and 2.4% sodium iodate in 47% of ethanol. Dilutions are made by diluting indicated volume with volume of normal urine. Readings were taken 1 minute after immersion.

| Dilution | 100% | 50% | 25% | 18% | 12% |
|---|---|---|---|---|---|
| Color | dark blue | dark blue | deep blue | purple | white |

EXAMPLE 4

Detection of Hydrogen Peroxide

The following concentrations were obtained by diluting certain volume part of aqueous 30% by weight of hydrogen peroxide solution with indicated volume parts of normal urine. Test strip was white before immersion into the testing solution. Readings were taken 5 minutes after immersion.

| Dilution | 2 parts/1 part H2O2/urine | 1 part/1 part H2O2/urine | 1 part/2 parts H2O2/urine |
|---|---|---|---|
| Color | light blue | slight blue | white |

EXAMPLE 5

Detection of Sodium Nitrite

The following concentrations were percentage by weight (w/w) in urine. Readings were taken 1 minute after immersion.

| Concentration | 10% | 5% | 1% | 0.5% | 0.1% | 005% | 0.01% |
|---|---|---|---|---|---|---|---|
| Color | very dark blue | dark blue | blue | light blue | light blue | very light blue | white |

Figure 2:
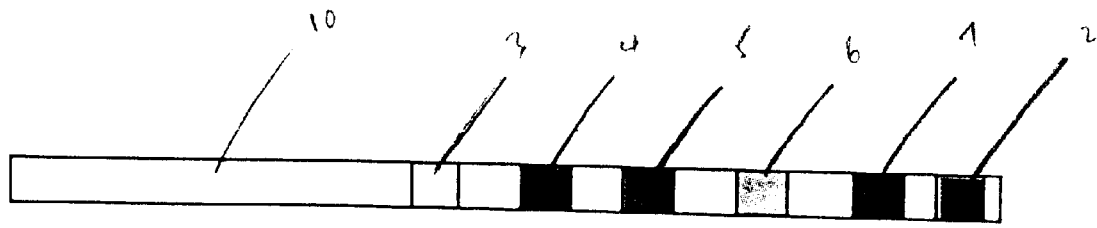
FIG. 2 is a perspective view of a commercial INTECT™ test strip for adulteration detection with tests for Creatinine, Nitrite, Glutaraldehyde, pH, Bleach and Specific Gravity.

Referring now to FIG. 2, a commercially available INTECT™ strip 10 is shown. The test strip can be used to test for adulteration of urine by Creatinine (3), Nitrite (4), Glutaraldehyde (5), pH (6), Specific Gravity (7), and Bleach (2).

Having described our invention, what we claim and desire by Letter Patent is:

1. A method for determining the presence of pyridimium chlorchromate or sodium nitrite, in urine samples, comprising:
   a) obtaining an aliquot of body fluid to be tested;
   b) contacting said bodily fluid with a dry test strip comprising a benzidine derivative; and
   c) determining the presence of pyridimium chlorochromate or sodium nitrite in the bodily fluid by performing color change observation on said test strip,
wherein a different color results for each particular oxidizing adulterant.

2. The method according to claim 1 wherein the benzidine derivative is in a range of 0.05 to 0.2 micromole/25 sq. mm.

3. The method according to claim 1 wherein the benzidine derivative is selected from the group consisting of o-tolidine, o-tolidine dihydrochloride, benzidine, benzidine dihydrochloride, 3,5,3',5'tetramethylbenzidine and 3,5,3', 5'tetramethylbenzidine dihydrochloride.

4. The method according to claim 1 wherein the adulterant is selected from the group consisting of sodium hypochlorite, chlorine, hydrogen peroxide, sodium bromide, iodine plus sodium iodide, pyridinium chlorochromate and sodium nitrite.

5. The method according to claim 1, wherein the bodily fluid is selected from the group consisting of urine, sweat, saliva and blood.

6. A method for determining the presence of pyridimium chlorchromate or sodium nitrite, in urine samples, comprising:
   a) obtaining an aliquot of body fluid to be tested;
   b) contacting said bodily fluid with a dry test strip comprising 3,5,3',5'tetramethylbenzidine; and
   c) determining the presence of pyridimium chlorochromate or sodium nitrite in the bodily fluid by performing color change observation on said test strip,
wherein a different color results for each particular oxidizing adulterant.

7. The method according to claim 6, wherein the 3,5,3', 5'tetramethylbenzidine is in a range of 0.05 to 0.2 micromole/25 sq. mm.

8. The method according to claim 6, wherein the adulterant is selected from the group consisting of sodium hypochlorite, chlorine, hydrogen peroxide, sodium bromide, iodine plus sodium iodide, pyridinium chlorochromate and sodium nitrite.

9. The method of claim 1, wherein the further clinical chemistry test is selected from the group consisting of enzyme immunoassay, lateral flow immunoassay, radioimmunoassay, and fluorescence polarization immunoassay.

10. The method of claim 6, wherein the further clinical chemistry test is selected from the group consisting of enzyme immunoassay, lateral flow immunoassay, radioimmunoassay, and fluorescence polarization immunoassay.

* * * * *